United States Patent [19]

Skjaerpe

[11] Patent Number: 4,501,274
[45] Date of Patent: Feb. 26, 1985

[54] MICROSURGICAL INSTRUMENT

[76] Inventor: Finn Skjaerpe, Nedreveien 1, Stavanger, Norway, N-4000

[21] Appl. No.: 438,891
[22] PCT Filed: Mar. 12, 1982
[86] PCT No.: PCT/NO82/00014
  § 371 Date: Oct. 29, 1982
  § 102(e) Date: Oct. 29, 1982
[87] PCT Pub. No.: WO82/03168
  PCT Pub. Date: Sep. 30, 1982

[30] Foreign Application Priority Data

Mar. 12, 1981 [NO] Norway .............................. 810849

[51] Int. Cl.³ .............................................. A61B 17/32
[52] U.S. Cl. ................................................... 128/305
[58] Field of Search ................... 128/303 R, 305, 304, 128/303.14, 751, 753, 754, 757; 30/124, 130, 172, 299, 279

[56] References Cited

U.S. PATENT DOCUMENTS

| | | | |
|---|---|---|---|
| 1,167,014 | 1/1916 | O'Brien | 128/751 X |
| 2,133,208 | 10/1938 | Nellis | 30/299 X |
| 2,668,536 | 2/1954 | Farries et al. | 128/305 |
| 3,185,155 | 5/1965 | Slaten et al. | 128/303 R |
| 4,315,511 | 2/1982 | Chin | 128/304 X |

FOREIGN PATENT DOCUMENTS 452338 12/1974 U.S.S.R. .............................. 128/305

Primary Examiner—Michael H. Thaler
Attorney, Agent, or Firm—Watson, Cole, Grindle & Watson

[57] ABSTRACT

A microsurgical instrument for performing selective trabeculectomy in surgical treatment of glaucoma includes a flexible probe (A) and a cutting member (C) fixed to the same. The cutting member comprises two knife blades (C1,C2) protruding in different directions from the probe and each providing at least one sharp edge (E1,E2) turned towards a free end of the probe.

The instrument is designed to be pulled between two incisions in the eye wall with the probe foremost through the Canal of Schlemm at the transition between cornea and sclera, thereby cutting away the inner wall of the canal and the corresponding part of the trabecular meshwork located in the canal. The aqueous humour of the eye then gains access to the outer wall of the Canal of Schlemm with its drainage outlets leading out of the eye.

13 Claims, 5 Drawing Figures

MICROSURGICAL INSTRUMENT

BACKGROUND OF THE INVENTION

The present invention relates to a microsurgical cutting instrument to be used in surgical treatment of glaucoma by means of a novel operational procedure, which significantly may be called "selective trabeculectomy".

Glaucoma is an ailment resulting in increased inner pressure in the eyeball. Within the eye, aqueous humor is produced at a fairly constant rate. This liquid is drained out through filterlike tissue (trabecular meshwork) in the area between iris and cornea into a collector canal running circularly along the transition between cornea and sclera (Canal of Schlemm), and from this canal through 20-30 drainage outlets in the eye wall into blood vessels (water veins).

The cause of glaucoma is believed to be a type of "clogging" of the trabecular meshwork, so that the outflow resistance increases. Then, also the pressure increases to allow the same volume of liquid to be drained out per time unit. All treatment aims at reducing the eye pressure. Such treatment is primarily medical, but when this is intolerable and/or insufficient, surgical treatment is used.

The surgical treatment may be subdivided according to three principles, namely:

1. Operations aiming at reduced production of aqueous humour.
2. Fistulizing procedures, i.e., surgical provision of artificial slits in the eye walls through which the liquid may seep out of the eye.
3. Operations on the trabecular meshwork. Existing procedures of this kind are of two types, i.e.:

(a) Approach through the anterior chamber of the eye by means of goniotomy or cautery of the trabecular meshwork with laser beams.

(b) Approach through the Canal of Schlemm. Such approach consists in opening this canal through a radial incision in the eye wall above the canal and insertion of a blunt probe or probe means with a cutting edge (trabeculotome). This instrument is then manipulated in such a way that it tears open or cuts through the trabecular meshwork into the anterior chamber of the eye. With such procedure a narrow slitlike opening is formed through the trabecular meshwork. Such slits exhibit, however, a considerable tendency to close.

SUMMARY OF THE INVENTION

In order to inhibit such closure it is an object of the present invention to provide a microsurgical instrument which through appropriate use may form a permanent opening from the anterior chamber of the eye to the Canal of Schlemm by selective removal of the inner wall of this canal along a certain sector. In this manner the aqueous humour gains direct access to the outer wall of the Canal of Schlemm, which has outlets or drainage canals, so that normal drainage of aqueous humour may be reestablished.

Thus, the invention concerns a microsurgical instrument for performing selective traveculectomy in surgical treatment of glaucoma, the instrument including flexible probe means and a cutting member fixed to the same. With this background the general inventive feature of the instrument is that the cutting member comprises two knife blades protruding in different directions from the probe and each providing at least one sharp cutting edge turned towards a free end of the probe means.

This instrument may be called a trabeculectome, as it is designed to be pulled through the Canal of Schlemm along a certain peripheral sector of the eye. By this the inner wall of the canal and the corresponding portion of the 0.1 mm thick trabecular meshwork are cut away.

As indicated, the trabeculectome consists of probe means and a cutting member. The probe means is preferably knob-shaped at the extreme end and made of flexible material, but this still sufficiently rigid to be inserted into and directed through the Canal of Schlemm. The cutting member has a double-cutting knife, the two cutting edges of which are angularly separated to such extent that the issuing V-form fits into the scleral groove in the eye wall, in which the trabecular meshwork is embedded. Advantageously, the cutting member is assymetrical in such a manner that the knife blade that projects perpendicularly into the anterior chamber towards the iris is short, whereas the blade that projects obliquely into the anterior chamber and forms a small angle with the back side of the cornea is longer. This feature stabilizes the correct position of the knife.

The probe means of the trabeculectome is directed through an incision in the eye wall into and along the Canal of Schlemm, and is pulled out through another incision at a certain distance from the first one. The cutting member of the trabeculectome is pulled after the probe means through the Canal of Schlemm with the two knife edges projecting into the anterior chamber of the eye and thereby cutting away a strip of the trabecular tissue and the inner wall of the Canal of Schlemm which are located between the cutting edges. This tissue strip is preferably removed together with the trabeculectome when it is pulled out through the second incision in the eye wall. Such removal of the tissue strip may be secured by mounting one or more hooks in the angle between the two knife edges in order to catch the cut away strip and carry it out of the eye.

The microsurgical instrument according to the invention allows a surgical procedure which secures a permanent, broad opening between the anterior chamber of the eye and the outlets from the Canal of Schlemm by removing the trabecular meshwork and the inner wall of the canal. Tissue removal together with maintained cell casing on the outer wall of the Canal of Schlemm make a closure of this opening improbable, even after a long period of time.

Experiences with this method up to now suggest a low rate of complications, so that the operational indications probably may be extended. This means that the patients may be operated at an earlier stage and thus expensive and troublesome medical treatment is avoided.

The invention will now be explained in more detail with reference to exemplified embodiments as shown in the accompanying drawings.

DETAILED DESCRIPTION OF THE PREFERRED EMBODIMENTS

Figure 1:
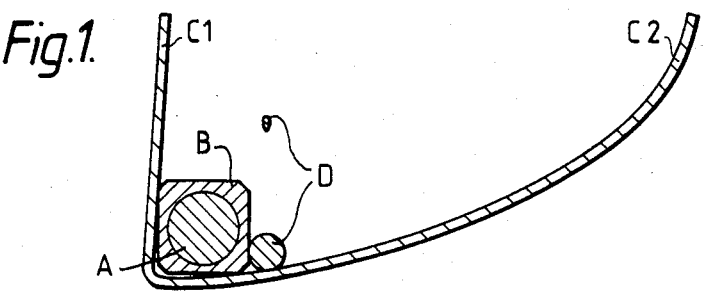
FIG. 1 shows a first embodiment of the instrument in a cross-section through the cutting member at a right angle to the longitudinal axis of the probe means.
Figure 2:
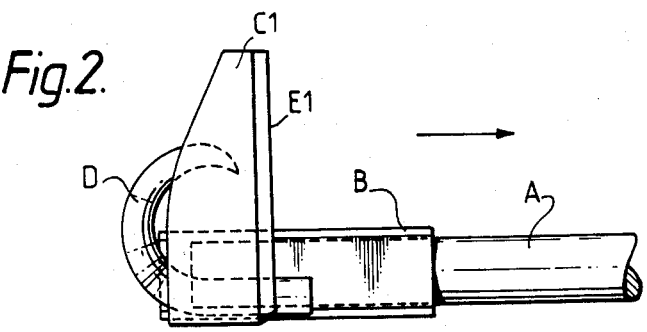
FIG. 2 is a side elevation of the instrument shown in FIG. 1.
Figure 3:
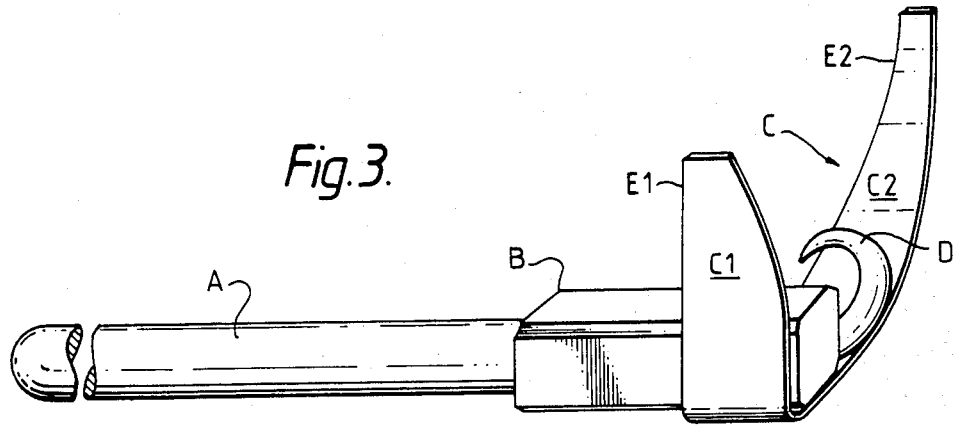
FIG. 3 shows the instrument in FIGS. 1 and 2 in perspective view.

The probe means A is in the embodiment shown in FIGS. 1–3 a monofilament of nylon, which is fused at one end to form a rounded knob. The other end of the probe is inserted into a hole in steel member B and rigidly clamped to this member. The knife member C is formed from a 1/100–5/100 mm thick stainless steel foil, which is finely sharpened at the front side E1 and bent into an approximate V-form adapted to the local anatomical features of the eye at the Canal of Schlemm and the trabecular meshwork. The member C is fixed to the member B and thereby also the probe A by means of a two-component epoxy glue. A point welding technique may also be used if the probe means is mounted on the member B after the welding step. An arrow above the probe in FIG. 2 shows the pulling direction in use. Between the knife blades a barbed hook D is fixed to the steel member B in order to catch the tissue strip which is cut free between the knives. This hook is also fastened by means of epoxy resin. Finally, a layer of epoxy resin is applied to the joints and transitions between the steel member B and the probe A to provide a completely smooth surface. Teflon and similar polymers may also be used as covering layer and silicone is considered particularly advantageous for this purpose.

Figure 4:
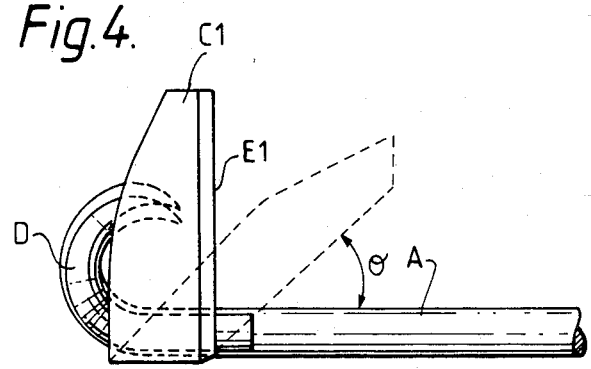
FIG. 4 is a side elevation of another embodiment of the instrument.
Figure 5:
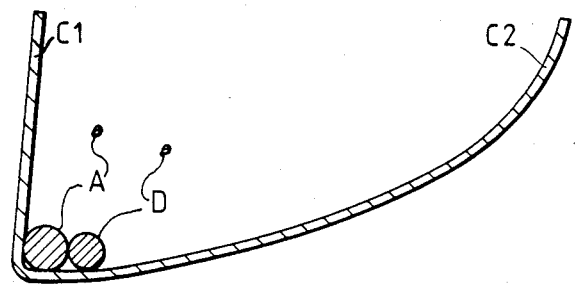
FIG. 5 shows a cross-section through the cutting member at a right angle to the longitudinal axis of the probe means in the embodiment of FIG. 4.

Another embodiment is illustrated in the FIGS. 4 and 5.

In this case the probe is made of flexible metal and welded to the knife member. The extreme rear end of the probe is bent forward between the knife blades to form a small sharp hook D. All joints are provided with a cover of epoxy resin and the probe is furnished with a layer of resin at the end to form a finely rounded knob.

Figure 6:
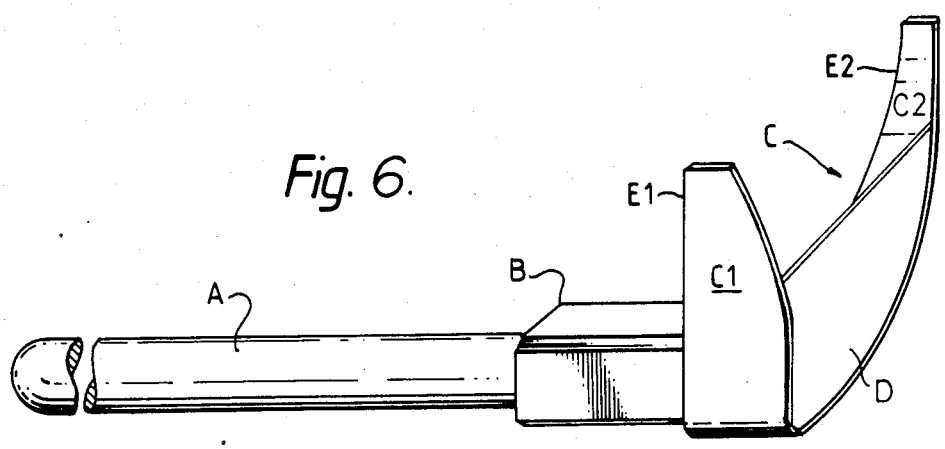
FIG. 6 shows a perspective view of a further embodiment of the inventive instrument.

The knife blades C1, C2 need not necessarily have a free end. Thus, the extreme ends of the knife blades may well be interconnected to form a closed knife blade ring, e.g., of approximate triangular shape. The cut-away tissue strip may then be captured by closing the rear opening of the knife ring, thereby catching the strip in the "container" thus formed. This embodiment of the inventive instrument is depicted in FIG. 6.

The instrument must necessarily be quite small to allow the intended surgical treatment of the eye. Thus, in the illustrated embodiments the probe has a diameter of approximately 0.25 mm and a length of the order of magnitude 4–8 cm and rather freely adaptable to the requirements of the eye surgeon. The shorter knife of the cutting member may suitably have a length of about 0.7–1.0 mm, while the longer, preferably curved knife may have a length of 1.5–1.8 mm. The width of the knives may be of the order of magnitude $0.3 \propto 0.5$ mm.

In the embodiments shown in the drawings and described above the cutting member is fixed at one end of the probe means. However, the cutting member may well be fixed to the probe at another location, e.g., on the central part of the same. The portion of the probe projecting from the rear side of the cutting member may then be used for improved steering of the instrument, when it is guided between the two incisions in the eye wall. If the cutting member is located approximately centrally on the probe, the protruding knife blades may further be provided with a cutting edge on both sides, so that the instrument may be effectively pulled in both directions through the Canal of Schlemm.

Although the cutting edges are shown in the drawing to form essentially right angles with the longitudinal axes of the probe means, the edges may also according to the invention advantageously be inclined at an angle of $\theta$ axis (see FIG. 4). This angle $\theta$ can vary from 45° to 90°. An inwards directed radial force is then exercised against the tissue strip during the movement of the cutting member through the Canal of Schlemm.

I claim:

1. A microsurgical instrument for performing selective trabeculectomy in the surgical treatment of glaucoma, said instrument including an elongated, flexible probe means having a first end and a second end, and a cutting member attached to said probe means at a point spaced apart from said first end, said cutting member including
    two knife blades which are separated so as to fit into the scleral groove of the eye wall in which trabecular meshwork is embedded and which protrude in different transverse directions from the probe means in order to extend from said groove into the anterior chamber of the eye, thus embracing a strip of said trabecular meshwork, each said knife blade providing a first edge which faces said first end of said probe means and a second edge which faces away from said first end of said cutting means, at least said first edge being sharp for cutting, and
    at least one catching device located between said two knife blades at a point spaced farther from said first end of said probe than said cutting edges of said knife blades, each catching device retaining thereon trabecular tissue which has been cut by said knife blades.

2. A microsurgical instrument as defined in claim 1, wherein a first blade of said two knife blades extends away from a longitudinal axis defined by said elongated probe means a distance less than second blade of said two knife blades, said first blade being flat and the second blade being curved so as to conform to the boundary surface of the tissue to be cut away.

3. A microsurgical instrument as defined in claim 1, wherein each catching device comprises a hook means which is curved toward the first end of said probe means.

4. A microsurgical instrument as defined in claim 1, wherein said two knife blades extend upwardly from a longitudinal axis defined by said elongated probe means at an angle $\theta$ of between 45° and 90°.

5. A microsurgical instrument as defined in claim 1, wherein said elongated probe means is made of a nylon monofilament and wherein said cutting member includes a metallic holder which is fixedly connected to said nylon monofilament.

6. A microsurgical instrument as defined in claim 5, wherein said knife blades and said catching devices are attached to said metallic holder.

7. A microsurgical instrument as defined in claim 1, wherein said elongated probe means is made of a flexible metallic material.

8. A microsurgical instrument as defined in claim 7, wherein said cutting means is welded to said elongated metallic probe means.

9. A microsurgical instrument as defined in claim 8, wherein said probe means is coated with a plastic material.

10. A microsurgical instrument as defined in claim 1, wherein said cutting member is attached to the second end of said elongated probe means.

11. A microsurgical instrument as defined in claim 1, wherein means are connected between the second edges of said knife blades to create a container area therebetween.

12. A microsurgical instrument as defined in claim 11, wherein said means connected between the second edges of said knife blades is a plate.

13. A microsurgical instrument as defined in claim 1, wherein said cutting member is made of a hard plastic material.

* * * * *